United States Patent [19]

Huss, Jr. et al.

[11] Patent Number: 5,030,785

[45] Date of Patent: Jul. 9, 1991

[54] PROCESS FOR PREPARING LONG CHAIN ALKYL AROMATIC COMPOUNDS EMPLOYING LEWIS ACID-PROMOTED ZEOLITE CATALYSTS

[75] Inventors: Albin Huss, Jr., Chadds Ford, Pa.; Quang N. Le, Cherry Hill, N.J.; Samuel A. Tabak, Wenonah, N.J.; Stephen S. Wong, Medford, N.J.

[73] Assignee: Mobil Oil Corp., Fairfax, Va.

[21] Appl. No.: 470,012

[22] Filed: Jan. 25, 1990

Related U.S. Application Data

[63] Continuation-in-part of Ser. No. 254,524, Oct. 6, 1988, Pat. No. 4,954,325, which is a continuation-in-part of Ser. No. 98,176, Sep. 18, 1987, abandoned, which is a continuation-in-part of Ser. No. 890,268, Jul. 29, 1986, abandoned.

[51] Int. Cl.$^5$ .............................. C07C 2/62; C07C 2/70
[52] U.S. Cl. ...................................... 585/456; 585/460; 585/463; 585/465; 585/467; 568/681
[58] Field of Search ............... 585/446, 459, 460, 465, 585/467, 456, 463

[56] References Cited

U.S. PATENT DOCUMENTS

| | | | |
|---|---|---|---|
| 2,904,607 | 9/1959 | Mattox et al. | 208/135 |
| 2,939,890 | 6/1960 | Hervert et al. | 585/463 |
| 3,131,230 | 4/1964 | Hervert et al. | 585/463 |
| 3,173,965 | 3/1965 | Pappas et al. | 585/254 |
| 3,251,897 | 5/1966 | Wise | 585/467 |
| 3,631,120 | 12/1971 | Eberly, Jr. et al. | 585/467 |
| 3,641,177 | 2/1972 | Eberly, Jr. et al. | 585/467 |
| 3,751,504 | 8/1973 | Keown et al. | 585/323 |
| 3,751,506 | 8/1973 | Burress | 502/77 |
| 4,035,308 | 7/1977 | Schenach | 585/24 |
| 4,148,834 | 4/1979 | Kennedy et al. | 585/449 |
| 4,301,316 | 11/1981 | Young | 585/455 |
| 4,301,317 | 11/1981 | Young | 585/467 |
| 4,319,067 | 3/1982 | Kreeger | 585/459 |
| 4,384,161 | 5/1983 | Huang | 585/331 |
| 4,439,409 | 3/1984 | Puppe et al. | 423/328 |
| 4,511,667 | 4/1985 | Mao et al. | 502/64 |
| 4,517,075 | 5/1985 | Dessau et al. | 585/459 |
| 4,551,573 | 11/1985 | Cobb | 585/459 |
| 4,691,068 | 9/1987 | Resh | 585/323 |
| 4,826,667 | 5/1989 | Zones et al. | 423/326 |
| 4,847,223 | 7/1989 | Le Van Mao et al. | 502/62 |

FOREIGN PATENT DOCUMENTS

| | | | |
|---|---|---|---|
| 0231860 | 8/1987 | European Pat. Off. | 502/64 |
| 0293032 | 11/1988 | European Pat. Off. | 502/64 |

Primary Examiner—Anthony McFarlane
Attorney, Agent, or Firm—Alexander J. McKillop; Charles J. Speciale; Dennis P. Santini

[57] ABSTRACT

Aromatic hydrocarbons are alkylated with relatively long chain alkylating agents, e.g., $C_6+$ olefins, in the presence of, as catalyst, certain Lewis acid-promoted zeolites to provide long chain aromatic products which are useful, inter alia, as lubricating oil stocks.

26 Claims, 1 Drawing Sheet

FIG. 1

PROCESS FOR PREPARING LONG CHAIN ALKYL AROMATIC COMPOUNDS EMPLOYING LEWIS ACID-PROMOTED ZEOLITE CATALYSTS

CROSS-REFERENCE TO RELATED APPLICATIONS

This application is a continuation-in-part of U.S. patent application Ser. No. 254,524, filed Oct. 6, 1988, which is now U.S. Pat. No. 4,954,325, which is a continuation-in-part of U.S. patent application Ser. No. 98,176, filed Sept. 18, 1987, now abandoned, which is a continuation-in-part of U.S. patent application Ser. No. 890,268, filed Jul. 29, 1986, now abandoned.

BACKGROUND OF THE INVENTION

This invention relates to a process for preparing long chain alkyl aromatic compounds by alkylating an aromatic compound with a relatively long chain alkylating agent employing a particular class of Lewis-acid promoted zeolites as alkylation catalysts.

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials have come to be known as "molecular sieves" and are utilized in a variety of ways to take advantage of these properties. Such molecular sieves, both natural and synthetic, include a wide variety of positive ion-containing crystalline silicates. These silicates can be described as a rigid three-dimensional framework of $SiO_4$ and Periodic Table Group IIIA element oxide, e.g., $AlO_4$, in which the tetrahedra are cross-linked by the sharing of oxygen atoms whereby the ratio of the total Group IIIA element, e.g., aluminum, and silicon atoms to oxygen atoms is 1:2. The electrovalence of the tetrahedra containing the Group IIIA element, e.g., aluminum, is balanced by the inclusion in the crystal of a cation, e.g., an alkali metal or an alkaline earth metal cation. This can be expressed wherein the ratio of the Group IIA element, e.g., aluminum, to the number of various cations, such as Ca/2, Sr/2, Na, K or Li, is equal to unity. One type of cation may be exchanged either entirely or partially with another type of cation utilizing ion exchange techniques in a conventional manner. By means of such cation exchange, it has been possible to vary the properties of a given silicate by suitable selection of the cation. The spaces between the tetrahedra are occupied by molecules of water prior to dehydration.

Prior art techniques have resulted in the formation of a great variety of synthetic zeolites. Many of these zeolites have come to be designated by letter or other convenient symbols, as illustrated by zeolite Z (U.S. Pat. No. 2,882,243); zeolite X (U.S. Pat. No. 2,882,244); zeolite Y (U.S. Pat. No. 3,130,007); zeolite ZK-5 (U.S. Pat. No. 3,247,195); zeolite ZK-4 (U.S. Pat. No. 3,314,752); zeolite ZSM-5 (U.S. Pat. No. 3,702,886); zeolite ZSM-11 (U.S. Pat. No. 3,709,979); zeolite ZSM-12 (U.S. Pat. No. 3,832,449); zeolite ZSM-20 (U.S. Pat. No. 3,972,983); zeolite ZSM-35 (U.S. Pat. No. 4,016,245); and zeolite ZSM-23 (U.S. Pat. No. 4,076,842), merely to name a few.

The $SiO_2/Al_2O_3$ ratio of a given zeolite is often variable. For example, zeolite X can be synthesized with $SiO_2/Al_2O_3$ ratios of from 2 to 3; zeolite Y, from 3 to about 6. In some zeolites, the upper limit of the $SiO_2/Al_2O_3$ ratio is unbounded. ZSM-5 is one such example wherein the $SiO_2/Al_2O_3$ ratio is at least 5 and up to the limits of present analytical measurement techniques. U.S. Pat. No. 3,941,871 (U.S. Pat. No. Re. 29,948) discloses a porous crystalline silicate made from a reaction mixture containing no deliberately added alumina in the recipe and exhibiting the X-ray diffraction pattern characteristic of ZSM-5. U.S. Pat. Nos. 4,061,724, 4,073,865 and 4,104,294 describe crystalline silicates of varying alumina and metal content.

The alkylation of aromatic hydrocarbon with olefin employing a Lewis acid or Friedel-Crafts catalyst, e.g., $AlCl_3$, $BF_3$, HF, etc., to provide alkyl aromatic compounds is known in the art. Thus, for example, the alkylation processes described in U.S. Pat. Nos. 2,939,890 and 3,131,230 utilize a catalyst composition containing $BF_3$ and a $BF_3$-modified substantially anhydrous inorganic oxide such as anhydrous gamma-alumina. U.S. Pat. No. 3,173,965 discloses the alkylation of benzene with olefin in the presence of a Friedel-Crafts catalyst, e.g., $AlCl_3$, $AlBr_3$, $FeCl_3$, $SnCl_4$, $BF_3$, $ZnCl_2$, HF, $H_2SO_4$, $P_2O_5$ and $H_3PO_4$, to provide a polyalkylated benzene product of relatively high viscosity index (V.I.), i.e., from 90 to 145, which is useful as a lubricant. According to U.S. Pat. No. 4,035,308, excess benzene is alkylated with decene dimer in the presence of $BF_3$-promoted anhydrous $AlCl_3$ to provide a monoalkyl benzene product useful as a lubricant or power transmission fluid. U.S. Pat. No. 4,148,834 describes a two-step alkylation process for preparing di-long chain alkyl aromatic compounds, useful as lubricants, in which aromatic hydrocarbon is alkylated with linear monoolefin in the presence of HF catalyst in a first step and aluminum chloride or aluminum bromide catalyst in a second step.

U.S. Pat. No. 4,691,068 discloses the preparation of long chain monoalkyl aromatics, useful in producing detergents, employing a Friedel-Crafts catalyst, e.g., $AlCl_3$-HCl, and featuring the recycle of a heavy boiling product fraction to the alkylation reaction.

With the aim of moving away from the use of strong acids as alkylation catalysts, the use of zeolites such as those referred to above has been investigated for the catalysis of aromatic hydrocarbon alkylation. Thus, the alkylation of aromatic hydrocarbons with an olefin in the presence of a zeolite having uniform pore openings of from about 6 to about 15 Angstrom units is described in U.S. Pat. No. 2,904,607. U.S. Pat. No. 3,251,897 describes the alkylation of aromatic hydrocarbons in the presence of X- or Y-type zeolites, specifically such type zeolites wherein the cation is a rare earth metal species and/or hydrogen. U.S. Pat. Nos. 3,751,504 and 3,751,506 describe the vapor phase alkylation of aromatic hydrocarbons with olefins, e.g., benzene with ethylene, in the presence of a ZSM-5 type zeolite catalyst. U.S. Pat. Nos. 3,631,120 and 3,641,177, describe a liquid phase process for the alkylation of aromatic hydrocarbons with olefins in the presence of certain zeolites. U.S. Pat. Nos. 4,301,316 and 4,301,317 disclose the use of such zeolites as ZSM-4, ZSM-20, ZSM-38, mazzite, Linde Type L and zeolite Beta to catalyze the alkylation of benzene with relatively long chain olefins to produce long chain alkylbenzenes.

U.S. Pat. No. 4,384,161 describes alkylation of isoparaffins with olefins over a Lewis acid-promoted large pore zeolite such as zeolite Beta, ZSM-4 and ZSM-20 to yield product having a large proportion of highly branched alkylates for blending into gasoline.

SUMMARY OF THE INVENTION

It is an object of this invention to provide a process for the alkylation of an aromatic compound with a relatively long chain alkylating agent to provide a long chain alkyl aromatic product employing as alkylation catalyst a Lewis acid-promoted zeolite possessing a Constraint Index, as defined infra, of not greater than about 5.

It is a particular object of the present invention to provide a process for producing predominantly 2- and 3-long chain alkylaromatics in which the aromatic ring is bonded to the alkylating agent predominantly in the 2- or 3-position of the latter.

It is another particular object of the invention to provide long chain alkylbenzenes which are useful, inter alia, as intermediates in the manufacture of synthetic detergents.

It is still another particular object of the present invention to provide a process for the alkylation of an aromatic hydrocarbon stream, e.g., one containing one or more of benzene, toluene, xylene, naphthalene, and the like, with a relatively long chain alkylating agent to produce an aromatic lube base stock of low pour and cloud point, high viscosity and improved thermal and oxidative stability properties.

By way of realizing the foregoing and other objects of the invention, a process for preparing long chain alkyl aromatic compounds is provided which comprises contacting at least one alkylatable aromatic compound with at least one alkylating agent possessing an alkylating aliphatic group having at least six carbon atoms under alkylation reaction conditions and in the presence of an alkylation catalyst to provide an alkylated aromatic product possessing at least one alkyl group derived from said alkylating agent, said catalyst comprising a Lewis acid-promoted zeolite possessing a Constraint Index of not greater than about 5.

DESCRIPTION OF SPECIFIC EMBODIMENTS

The entire contents of U.S. applications Ser. Nos. 254,524; 98,176; and 890,268 are incorporated herein by reference.

The term "aromatic" in reference to the alkylatable compounds which are useful herein is to be understood in accordance with its art-recognized scope which includes alkyl substituted and unsubstituted mono- and polynuclear compounds. Compounds of an aromatic character which posses a hetero atom are also useful provided they do not act as catalyst poisons under the reaction conditions selected.

Substituted aromatic compounds which can be alkylated herein must possess at least one hydrogen atom directly bonded to the aromatic nucleus. The aromatic rings can be substituted with one or more alkyl, aryl, alkaryl, alkoxy, aryloxy, cycloalkyl, halide, and/or other groups which do not interfere with the alkylation reaction.

Suitable aromatic hydrocarbons include benzene, naphthalene, anthracene, naphthacene, perylene, coronene and phenanthrene.

Generally the alkyl groups which can be present as substituents on the aromatic compound contain from one to about 22 carbon atoms and preferably from about one to eight carbon atoms, and most preferably from about one to four carbon atoms.

Suitable alkyl substituted aromatic compounds include toluene, xylene, isopropylbenzene, normal propylbenzene, alpha-methylnaphthalene, ethylbenzene, cumene, mesitylene, durene, p-cymene, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic hydrocarbons can also be used as starting materials and include aromatic hydrocarbons such as are produced by the alkylation of aromatic hydrocarbons with olefin oligomers. Such product are frequently referred to in the art as alkylate and include hexylbenzene, nonylbenzene, dodecylbenzene, pentadecylbenzene, hexyltoluene, nonyltoluene, dodecyltoluene, pentadecytoluene, etc. Very often alkylate is obtained as a high boiling fraction in which the alkyl group attached to the aromatic nucleus varies in size from about $C_6$ to about $C_{12}$.

Reformate containing substantial quantities of benzene, toluene and/or xylene constitutes a particularly useful feed for the alkylation process of this invention.

The alkylating agents which are useful in the process of this invention generally include any aliphatic or aromatic organic compound having one or more available alkylating aliphatic groups capable of reaction with the alkylatable aromatic compound. The alkylatable group itself should have at least about 6 carbon atoms, preferably at least about 8, and still more preferably at least about 12 carbon atoms. Examples of suitable alkylating agents are olefins such as hexenes, heptenes, octenes, nonenes, decenes, undecenes, dodecenes, and the like; alcohols (inclusive of monoalcohols, dialcohols, trialcohols, etc.) such as hexanols, heptanols, octanols, nonanols, decanols, undecanols and dodecanols; and alkyl halides such as hexyl chlorides, octyl chlorides, dodecyl chlorides; and, higher homologs of the foregoing. Branched alkylating agents, especially oligomerized olefins such as the trimers, tetramers, pentamers, etc., of light olefins such as ethylene, propylene, the butylenes, etc., are also useful herein.

The zeolite catalysts which are useful in the alkylation process of this invention are those possessing a Constraint Index of not greater than about 5 and preferably not greater than about 3. The method by which Constraint Index is determined is described fully in U.S. Pat. No. 4,016,218, incorporated herein by reference for details of the method. Constraint Index (CI) values for some typical zeolites including some which are suitable as catalysts in the aromatic alkylation process of this invention are:

|  | CI (at test temperature) |
|---|---|
| ZSM-4 | 0.5 (316° C.) |
| ZSM-5 | 6-8.3 (371° C.-316° C.) |
| ZSM-11 | 5-8.7 (371° C.-316° C.) |
| ZSM-12 | 2.3 (316° C.) |
| ZSM-20 | 0.5 (371° C.) |
| ZSM-22 | 7.3 (427° C.) |
| ZSM-23 | 9.1 (427° C.) |
| ZSM-34 | 50 (371° C.) |
| ZSM-35 | 4.5 (454° C.) |
| ZSM-48 | 3.5 (538° C.) |
| ZSM-50 | 2.1 (427° C.) |
| MCM-22 | 1.5 (454° C.) |
| TMA Offretite | 3.7 (316° C.) |
| TEA Mordenite | 0.4 (316° C.) |
| Clinoptilolite | 3.4 (510° C.) |
| Mordenite | 0.5 (316° C.) |
| REY | 0.4 (316° C.) |
| Amorphous Silica-alumina | 0.6 (538° C.) |
| Dealuminized Y | 0.5 (510° C.) |
| Erionite | 38 (316° C.) |
| Zeolite Beta | 0.6-2.0 (316° C.-399° C.) |

The above-described Constraint Index is an important and even critical definition of those zeolites which are useful in the aromatic alkylation process of the present invention. The very nature of this parameter and the above-referenced procedure by which it is determined, however, admits of the possibility that a given zeolite can be tested under somewhat different conditions and thereby exhibit different Constraint Indices. Constraint Index appears to vary somewhat with the severity of the conversion operation and the presence or absence of binder material. Similarly, other variables such as crystal size of the zeolite, the presence of occluded contaminants, etc., may affect the observed Constraint Index value. It will therefore be appreciated that it may be possible to select test conditions, e.g., temperature, as to establish more than one value for the Constraint Index of a particular zeolite. This explains the range of Constraint Indices for some zeolites, such as ZSM-5, ZSM-11 and Beta.

It is to be realized that the above CI values typically characterize the specified zeolites but that such are the cumulative result of several variables useful in the determination and calculation thereof. Thus, for a given zeolite exhibiting a CI value within the range of 5 or less, depending on the temperature employed during the test method within the range of 290° C. to about 538° C., with accompanying conversion between 10% and 60%, the CI may vary within the indicated range of 5 or less. Accordingly, it will be understood to those skilled in the art that the CI as utilized herein, while affording a highly useful means for characterizing the zeolites of interest, is approximate taking into consideration the manner of its determination including the possibility in some instances of compounding variable extremes. However, in all instances, at a temperature within the above-specified range of 290° C. to about 538° C., the CI will have a value for any given zeolite of interest herein of not greater than about 5 and preferably not greater than about 3.

Some zeolite catalysts which are useful in the process of this invention include zeolites ZSM-4, ZSM-12, ZSM-20, ZSM-35, ZSM-48, ZSM-50, MCM-22, TMA offretite, TEA mordenite, clinoptilolite, mordenite, REY and zeolite Beta. Of these, zeolites ZSM-12, MCM-22 and Beta are preferred and zeolite MCM-22 is particularly preferred.

Zeolite ZSM-4 is taught in British Patent No. 1,117,568; ZSM-12 in U.S. Pat. No. 3,832,449; ZSM-20 in U.S. Pat. No. 3,972,983; ZSM-35 in U.S. Pat. No. 4,016,245; ZSM-48 in U.S. Pat. No. 4,397,827; ZSM-50 in U.S. Pat. No. 4,640,849; and Beta in U.S. Pat. No. 3,308,069, each incorporated herein by reference.

The definitive characteristics of zeolite MCM-22, and in particular its x-ray diffraction pattern, together with a detailed description of its synthesis, are set forth below.

In its calcined form, synthetic porous crystalline MCM-22 has an X-ray diffraction pattern including the following lines:

TABLE A

| Interplanar d-Spacing (A) | Relative Intensity, $I/I_o \times 100$ |
|---|---|
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

MCM-22 may be characterized by an X-ray diffraction pattern in its calcined form including the following lines:

TABLE B

| Interplanar d-Spacing (A) | Relative Intensity, $I/I_o \times 100$ |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

More specifically, the calcined form has an X-ray diffraction pattern including the following lines:

TABLE C

| Interplanar d-Spacing (A) | Relative Intensity, $I/I_o \times 100$ |
|---|---|
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

Most specifically, it may be characterized in its calcined form by an X-ray diffraction pattern including the following lines:

TABLE D

| Interplanar d-Spacing (A) | Relative Intensity, $I/I_o \times 100$ |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensites, 100 $I/I_o$, where $I_o$ is the intensity of the strongest line or peak, and d (obs.) the interplanar spacing in Angstrom Units (A), corresponding to the recorded lines, were determined. In Tables A-D, the relative intensities are give in terms of the symbols W=weak, M=medium, S=strong, VS=very strong. In terms of intensities, these may be generally designated as follows:

W=0-20
M=20-40
S=40-60
VS=60-100

It should be understood that these X-ray diffraction patterns are characteristic of all species of the zeolite. The sodium form as well as other cationic forms reveal substantially the same pattern with some minor shifts in interplanar spacing and variation in relative intensity. Other minor variations can occur depending on the ratio of structural components, e.g. silicon to aluminum mole ratio of the particular sample, as well as its degree of thermal treatment.

Zeolite MCM-22 has a composition involving the molar relationship:

$$X_2O_3:(n)YO_2,$$

wherein X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In the as-synthesized form, zeolite MCM-22 has a formula, on an anhydrous basis and in terms of moles of oxides per n moles of $YO_2$, as follows:

$$(0.005-0.1)Na_2O:(1-4)R:X_2O_3:nYO_2$$

wherein R is an organic component. The Na and R components are associated with the zeolite as a result of their presence during crystallization, and are easily removed by post-crystallization methods hereinafter more particularly described.

Zeolite MCM-22 is thermally stable and exhibits a high surface area greater than about 400 m²/gm as measured by the BET (Bruenauer, Emmet and Teller) test and unusually large sorption capacity when compared to previously described crystal structures having similar X-ray diffraction patterns. As is evident from the above formula, MCM-22 is synthesized nearly free of Na cations and thus possesses acid catalysis activity as synthesized. It can, therefore, be used as a component of the alkylation catalyst composition herein without having to first undergo an exchange step. To the extent desired, however, the original sodium cations of the as-synthesized material can be replaced in accordance with techniques well known in the art, at least in part, by ion exchange with other cations. Preferred replacement cations include metal ions, hydrogen ions, hydrogen precursor, e.g., ammonium, ions and mixtures thereof. Particularly preferred cations are those which tailor the activity of the catalyst for the present process. These include hydrogen, rare earth metals and metals of Groups IIA, IIIA, IVA, IB, IIB, IIIB, IVB and VIII of the Periodic Table of the Elements.

In its calcined form, zeolite MCM-22 appears to be made up of a single crystal phase with little or no detectable impurity crystal phases and has an X-ray diffraction pattern including the lines listed in above Tables A-D.

Zeolite MCM-22 can be prepared from a reaction mixture containing sources of alkali or alkaline earth metal (M), e.g., sodium or potassium, cation, an oxide of trivalent element X, e.g., aluminum, an oxide of tetravalent element Y, e.g., silicon, an organic (R) directing agent, hereinafter more particularly described, and water, said reaction mixture having a composition, in terms of mole ratios of oxides, within the following ranges:

| Reactants | Useful | Preferred |
|---|---|---|
| $YO_2/X_2O_3$ | 10-60 | 10-40 |
| $H_2O/YO_2$ | 5-100 | 10-50 |
| $OH^-/YO_2$ | 0.01-1.0 | 0.1-0.5 |
| $M/YO_2$ | 0.01-2.0 | 0.1-1.0 |
| $R/YO_2$ | 0.05-1.0 | 0.1-0.5 |

In a preferred method of synthesizing zeolite MCM-22, the $YO_2$ reactant contains a substantial amount of solid $YO_2$, e.g., at least about 30 wt. % solid $YO_2$. Where $YO_2$ is silica, the use of a silica source containing at least about 30 wt. % solid silica, e.g., Ultrasil (a precipitated, spray dried silica containing about 90 wt. % silica) or HiSil (a precipitated hydrated $SiO_2$ containing about 87 wt. % silica, about 6 wt. % free $H_2O$ and about 4.5 wt. % bound $H_2O$ of hydration and having a particle size of about 0.02 micron) favors crystal formation from the above mixture. If another source of oxide of silicon, e.g., Q-Brand (a sodium silicate comprised of about 28.8 wt. % of $SiO_2$, 8.9 wt. % $Na_2O$ and 62.3 wt. % $H_2O$) is used, crystallization may yield little if any MCM-22 crystalline material and impurity phases of other crystal structures, e.g., ZSM-12, may be produced. Preferably, therefore, the YO$_2$, e.g., silica, source contains at least about 30 wt. % solid YO$_2$, e.g., silica, and more preferably at least about 40 wt. % solid YO$_2$, e.g., silica.

Crystallization of the MCM-22 crystalline material can be carried out at either static or stirred conditions in a suitable reactor vessel such as, e.g., polypropylene jars or teflon-lined or stainless steel autoclaves. The total useful range of temperatures for crystallization is from about 80° C. to about 225° C. for a time sufficient for crystallization to occur at the temperature used, e.g., from about 25 hours to about 60 days. Thereafter, the crystals are separated from the liquid and recovered.

The organic directing agent for use in synthesizing zeolite MCM-22 from the above reaction mixture is hexamethyleneimine.

It should be realized that the reaction mixture components can be supplied by more than one source. The reaction mixture can be prepared either batchwise or continuously. Crystal size and crystallization time of the MCM-22 crystalline material will vary with the nature of the reaction mixture employed and the crystallization conditions.

In all cases, synthesis of the MCM-22 crystals is facilitated by the presence of at least about 0.01 percent, preferably about 0.10 percent and still more preferably about 1 percent, seed crystals (based on total weight) of the crystalline product.

The zeolites for use herein can be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be introduced in the catalyst composition by way of co-crystallization, exchanged into the composition to the extent a Group IIIA element, e.g., aluminum, is in the structure, impregnated therein or intimately physically admixed therewith. Such component can be impregnated in, or on, the zeolite such as, for example, by, in the case of platinum, treating the zeolite with a solution containing a platinum metal-containing ion. Thus, suitable platinum compounds for this purpose include chloroplatinic acid, platinous chloride and various compounds containing the platinum amine complex.

The useful zeolites, especially in their metal, hydrogen and ammonium forms, can be beneficially converted to another form by thermal treatment. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience. The thermal treatment can be performed at a temperature of up to about 925° C.

Prior to their use in the aromatic alkylation process of this invention, the zeolite crystals should be dehydrated, at least partially. This can be done by heating the crystals to a temperature in the range of from about 200° C. to about 595° C. in an inert atmosphere, such as air, nitrogen, etc. and at atmospheric, subatmospheric or superatmospheric pressures for between about 30 minutes to about 48 hours. Dehydration can also be performed at room temperature merely by placing the crystalline material in a vacuum, but a longer time is required to obtain a sufficient amount of dehydration.

The zeolites employed herein can be shaped into a wide variety of particle sizes. Generally speaking, the particles can be in the form of a powder, a granule, or a molded product such as an extrudate having a particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

It may be desired to incorporate the selected zeolite catalyst with another material which is resistant to the temperatures and other conditions employed in the process of this invention. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a meterial in conjunction with the catalyst zeolite, i.e., combined therwith or present during its synthesis, which itself is catalytically active may change the conversion and/or selectivity of the catalyst. Inactive materials suitably serve as diluents to control the amount of conversion so that aromatic alkanol products can be obtained economically and orderly without employing other means for controlling the rate of reaction. These materials may be incorporated into naturally occurring clays, e.g., bentonite and kaolin, to improve the crush strength of the catalyst under commercial alkylation operating conditions. Said materials, i.e., clays, oxides, etc., function as binders for the catalyst. It is desirable to provide a catalyst having good crush strength because in commercial use, it is desirable to prevent the catalyst from breaking down into powder-like materials. These clay binders have been employed normally only for the purpose of improving the crush strength of the catalyst.

Naturally occurring clays which can be composited with the zeolite catalyst herein include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with zeolite also include inorganic oxides, notably alumina.

In addition to the foregoing materials, the zeolite catalyst can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia. It may also be advantageous to provide at least a part of the foregoing matrix materials in colloidal form so as to facilitate extrusion of the bound catalyst component(s).

The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

The stability of the alkylation catalyst of the invention may be increased by steaming. U.S. Pat. Nos. 4,663,492; 4,594,146; 4,522,929; and 4,429,176, the entire disclosures of which are incorporated herein by reference, describe conditions for the steam stabilization of zeolite catalysts which can be utilized to steam-stabilize the catalyst for use herein. The steam stabilization conditions include contacting the catalyst with, e.g., 5–100% steam at a temperature of at least about 300° C. (e.g., 300°–650° C.) for at least one hour (e.g., 1–200 hours) at a pressure of 101–2,500 kPa. In a more particular embodiment, the catalyst can be made to undergo steaming with 75–100% steam at 315°–500° C. and atmospheric pressure for 2–25 hours. In accordance with the steam stabilization treatment described in the above-mentioned patents, the steaming of the catalyst can take place under conditions sufficient to initially increase the Alpha Value of the catalyst, the significance of which is discussed infra, and produce a steamed catalyst having a peak Alpha Value. If desired, steaming can be continued to subsequently reduce the Alpha Value from the peak Alpha Value to an Alpha Value which is substantially the same as the Alpha Value of the unsteamed catalyst.

As previously indicated, the zeolite alkylation catalyst herein is associated with a Lewis acid-promoter. A Lewis acid is generally considered to be a molecule which is capable of combining with another molecule or ion by forming a covalent chemical bond with two electrons from the second molecule or ion, which is to say, a Lewis acid is an electron acceptor. Examples of Lewis acids include boron trifluoride ($BF_3$), antimony pentafluoride ($SbF_5$) and aluminum chloride ($AlCl_3$). The present invention contemplates the use of these and all other Lewis acids including those disclosed in "Friedel-Crafts and Related Reactions", Interscience Publishers, Chapters III and IV (1963), the contents of which are incorporated by reference herein. $BF_3$ is a preferred Lewis acid for use in the alkylation process of this invention. In the case of $BF_3$, this promoter is preferably present in the alkylation zone in an amount which exceeds that required to saturate the zeolite catalyst component considered not only as the zeolite per se but as any other material, e.g., binder or matrix material, which might be associated therewith.

The alkylation process of this invention is conducted such that the organic reactants, i.e., the alkylatable aromatic compound and the alkylating agent, are brought into contact with the zeolite catalyst composition in a suitable reaction zone such as, for example, in a flow reactor containing a fixed bed of the catalyst composition, under effective alkylation conditions. Such conditions include a temperature of from about −40° C. to about 250° C., a pressure of from about 0.2 to about 25 atmospheres, a feed weight hourly space velocity (WHSV) of from about 0.01 $hr^{-1}$ to about 500 $hr^{-1}$ and an alkylatable aromatic compound to alkylating agent mole ratio of from about 0.1:1 to about 50:1. The WHSV is based upon the weight of the zeolite catalyst composition employed, i.e., the total weight of active zeolite catalyst (and binder if present). Preferred reaction conditions include a temperature within the approximate range of from about −20° C. to about 150° C., a pressure of from about 1 to about 20 atmospheres, a WHSV of from about 0.1 to about 100 and an alkylatable aromatic compound to alkylating agent mole ratio of from about 0.5:1 to about 5:1. The reactants can be in either the vapor phase or the liquid phase can be neat, i.e., free from intentional admixture or dilution with other material, or they can be brought into contact with the zeolite catalyst composition with the aid of carrier gases or diluents such as, for example, hydrogen or nitrogen.

The alkylation process herein can be carried out as a batch-type, semi-continuous or continuous operation utilizing a fixed or moving bed catalyst system. A preferred embodiment entails use of a catalyst zone wherein the hydrocarbon charge is passed concurrently or countercurrently through a moving bed of particle-form catalyst. The latter, after use, is conducted to a regeneration zone where coke is burned from the catalyst in an oxygen-containing atmosphere (such as air) at elevated temperature, after which the regenerated catalyst is recycled to the conversion zone for further contact with the organic reactants.

The present alkylation process can be conducted with the addition of water to the alkylation reactor, e.g., at a rate of from about 0.1 ppmw to about 1 wt %, based upon total hydrocarbon feed rate, preferably at a rate of from about 0.1 ppmw to about 500 ppmw. The water can be supplied as such or as a feed material which produces water under the alkylation conditions selected. Suitable water-producing materials which can be introduced into the reactor without interfering with the desired alkylation include monohydric and dihydric alcohols which yield water upon undergoing dehydration. Of this group, particular preference is accorded the aliphatic alcohols, especially those containing 1 to 6 carbon atoms as, for example, methanol, ethanol, isopropanol, t-butyl alcohol and isopentyl alcohol. The optional water and/or water-producing material can be added directly to the reactor, e.g., with the feed, and/or it can be incorporated into the zeolite, either by direct contact therewith or by exposing the zeolite to an atmosphere of water and/or water-producing material. For example, when the added water and/or water-producing material is pre-introduced into the zeolite, the amount of water and/or water-producing material taken up by the zeolite can be made to vary from about 0.5 to about 25, and preferably from about 1 to about 10, weight percent of the catalyst.

Figure 1:
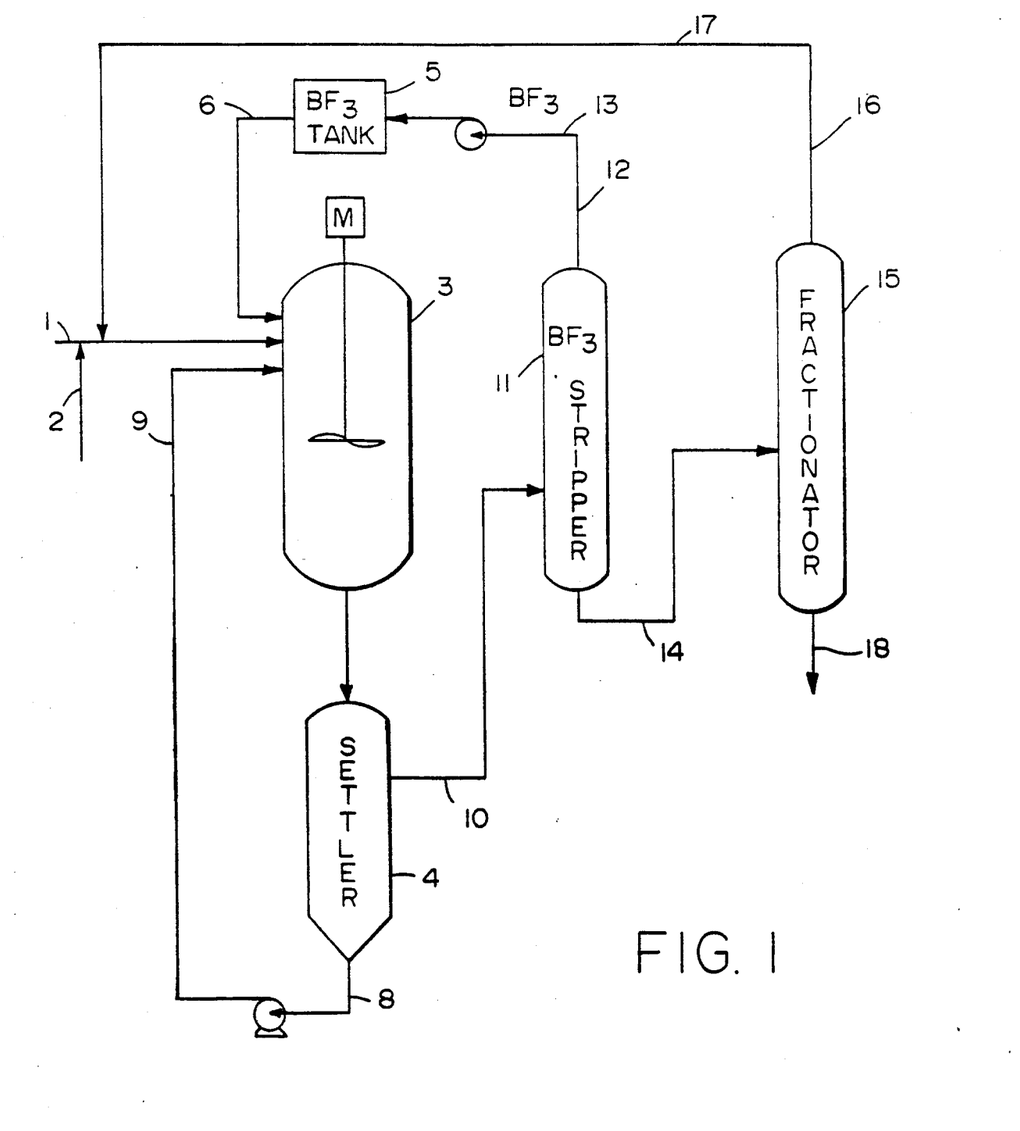
FIG. 1 is a block flow diagram of one embodiment of the aromatic alkylation process of the present invention.

A suitable system for carrying out the aromatic alkylation process of this invention on a continuous basis is shown in FIG. 1. A stream containing benzene and $C_{16}$ alpha olefin is introduced through line 1 into stirred reactor 3 containing zeolite. Optionally, water and/or a water-producing material such as methanol is introduced through line 2 into the reactor. $BF_3$ is introduced as needed from holding tank 5 through line 6 into the reactor. The amount of $BF_3$ introduced is such as to exceed that which is required to saturate the zeolite (as well as any binder or matrix material with which the zeolite might be composited). Zeolite slurry is removed from the reactor and is introduced to settling 4, the recovered zeolite thereafter being recycled to the alkylation reactor via line 9. The hydrocarbon product mixture is removed from the settling vessel through line 10 and introduced into $BF_3$ stripper 11 from which $BF_3$ is removed as overhead through line 12 and recycled through line 13 to $BF_3$ holding tank 5. The remaining hydrocarbon product mixture is withdrawn from the $BF_3$ stripper and passes through line 14 into fractionator 15 where unreacted $C_{16}$ alpha olefin is removed as overhead through line 16 and recycled through line 17 to reactant feed stream line 1. Desired alkylated benzene product is withdrawn from the bottom of fractionator 15 through line 18.

In order to more fully illustrate the alkylation process of this invention and the manner of practicing same, the following examples are presented. In examples illustrative of the synthesis of zeolite, whenever sorption data are set forth for comparison of sorptive capacities for water, cyclohexane and/or n-hexane, they were Equilibrium Adsorption values determined as follows:

A weighed sample of the calcined adsorbent was contacted with the desired pure adsorbate vapor in an adsorption chamber, evacuated to less than 1 mm Hg and contacted with 12 Torr of water vapor or 40 Torr of n-hexane or 40 Torr of cyclohexane vapor, pressures less than the vapor-liquid equilibrium pressure of the respective adsorbate at 90° C. The pressure was kept constant (within about ±0.5 mm Hg) by addition of adsorbate vapor controlled by a manostat during the adsorption period, which did not exceed about 8 hours. As adsorbate was adsorbed by the crystalline material, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample in g/100 g of calcined adsorbant. Zeolite MCM-22 always exhibits Equilibrium Adsorption values of greater than about 10 wt.% for water vapor, greater than about 4.5 wt. %, usually greater than about 7 wt. % for cyclohexane vapor and greater than about 10 wt. % for n-hexane vapor. These vapor sorption capacities are a notable distinguishing feature of zeolite MCM-22 and are preferred for the zeolite component of catalyst for use herein.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 (Rate Constant = 0.016 sec $^{-1}$). The Alpha Test is described in U.S. Pat. No. 3,354,078, in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395.

EXAMPLE 1

One part of sodium aluminate (43.5% $Al_2O_3$, 32.2% $Na_2O$, 25.6% $H_2O$) was dissolved in a solution containing 1 part of 50% NaOH solution and 103.13 parts $H_2O$. To this was added 4.50 parts hexamethyleneimine. The resulting solution was added to 8.55 parts of Ultrasil, a precipitated, spray-dried silica (about 90% $SiO_2$).

The reaction mixture had the following composition, in mole ratios:

$SiO_2/Al_2O_3 = 30.0$
$OH^-/SiO_2 = 0.18$
$H_2O/SiO_2 = 44.9$  $Na/SiO_2 = 0.18$
$R/SiO_2 = 0.35$ where R is hexamethyleneimine.

The mixture was crystallized in a stainless steel reactor, with stirring, at 150° C. for 7 days. The crystalline product was filtered, washed with water and dried at 120° C. After a 20 hour calcination at 538° C., the X-ray diffraction pattern contained the major lines listed in Table E. The sorption capacities of the calcined material were measured to be:

$H_2O$: 15.2 wt. %
Cyclohexane: 14.6 wt. %
n-Hexane: 16.7 wt. %

The surface area of the calcined crystalline material was measured to be 494 $m^2/g$.

The chemical composition of the uncalcined material was determined to be as follows:

| Component | wt. % |
|---|---|
| $SiO_2$ | 66.9 |
| $Al_2O_3$ | 5.40 |
| Na | 0.03 |
| N | 2.27 |
| Ash | 76.3 |
| $SiO_2/Al_2O_3$, mole ratio = 21.1 | |

TABLE E

| Degrees 2-Theta | Interplanar d-Spacing (A) | $I/I_o$ |
|---|---|---|
| 2.80 | 31.55 | 25 |
| 4.02 | 21.98 | 10 |
| 7.10 | 12.45 | 96 |
| 7.95 | 11.12 | 47 |
| 10.00 | 8.85 | 51 |
| 12.90 | 6.86 | 11 |
| 14.34 | 6.18 | 42 |
| 14.72 | 6.02 | 15 |
| 15.90 | 5.57 | 20 |
| 17.81 | 4.98 | 5 |
| 20.20 | 4.40 | 20 |
| 20.91 | 4.25 | 5 |
| 21.59 | 4.12 | 20 |
| 21.92 | 4.06 | 13 |
| 22.67 | 3.92 | 30 |
| 23.70 | 3.75 | 13 |
| 24.97 | 3.57 | 15 |
| 25.01 | 3.56 | 20 |
| 26.00 | 3.43 | 100 |
| 26.69 | 3.31 | 14 |
| 27.75 | 3.21 | 15 |
| 28.52 | 3.13 | 10 |
| 29.01 | 3.08 | 5 |
| 29.71 | 3.01 | 5 |
| 31.61 | 2.830 | 5 |
| 32.21 | 2.779 | 5 |
| 33.35 | 2.687 | 5 |
| 34.61 | 2.592 | 5 |

EXAMPLE 2

A portion of the calcined crystalline product of Example 1 was tested in the Alpha Test and was found to have an Alpha Value of 224.

EXAMPLES 3-5

Three separate synthesis reaction mixtures were prepared with compositions indicated in Table F. The mixtures were prepared with sodium aluminate, sodium hydroxide, Ultrasil, hexamethyleneimine (R) and water. The mixtures were maintained at 150° C., 143° C. and 150° C., respectively, for 7, 8 and 6 days respectively in stainless steel autoclaves at autogenous pressure. Solids were separated from any unreacted components by filtration and then water washed, followed by drying at 120° C. The product crystals were analyzed by X-ray diffraction, sorption, surface area and chemical analyses. Results of the sorption, surface area and chemical analyses are presented in Table F. The sorption and surface area measurements were of the calcined product.

TABLE F

| Example | 3 | 4 | 5 |
|---|---|---|---|
| Synthesis Mixture, mole ratios | | | |
| $SiO_2/Al_2O_3$ | 30.0 | 30.0 | 30.0 |
| $OH^-/SiO_2$ | 0.18 | 0.18 | 0.18 |
| $H_2O/SiO_2$ | 19.4 | 19.4 | 44.9 |
| $Na/SiO_2$ | 0.18 | 0.18 | 0.18 |
| $R/SiO_2$ | 0.35 | 0.35 | 0.35 |
| Product Composition, Wt. % | | | |
| $SiO_2$ | 64.3 | 68.5 | 74.5 |
| $Al_2O_3$ | 4.85 | 5.58 | 4.87 |
| Na | 0.08 | 0.05 | 0.01 |
| N | 2.40 | 2.33 | 2.12 |
| Ash | 77.1 | 77.3 | 78.2 |
| $SiO_2/Al_2O_3$, mole ratio | 22.5 | 20.9 | 26.0 |
| Adsorption, Wt. % | | | |
| $H_2O$ | 14.9 | 13.6 | 14.6 |
| Cyclohexane | 12.5 | 12.2 | 13.6 |
| n-Hexane | 14.6 | 16.2 | 19.0 |
| Surface Area, $m^2/g$ | 481 | 492 | 487 |

EXAMPLE 6

Quantities of the calcined (538° C. for 3 hours) crystalline silicate products of Examples 3, 4 and 5 were tested in the Alpha Test and found to have Alpha Values of 227, 180 and 187, respectively.

EXAMPLE 7

To demonstrate a further preparation of the present zeolite, 4.49 parts of hexamethyleneimine was added to a solution containing 1 part of sodium aluminate, 1 part of 50% NaOH solution and 44.19 parts of $H_2O$. To the combined solution were added 8.54 parts of Ultrasil silica. The mixture was crystallized with agitation at 145° C. for 59 hours and the resultant product was water washed and dried at 120° C.

Product chemical composition, surface area and adsorption analyses results are set forth in Table G:

TABLE G

| Product Composition (uncalcined) | |
|---|---|
| C | 12.1 wt. % |
| N | 1.98 wt. % |
| Na | 640 ppm |
| $Al_2O_3$ | 5.0 wt. % |
| $SiO_2$ | 74.9 wt. % |
| $SiO_2/Al_2O_3$, mole ratio | 25.4 |
| Adsorption, wt. % | |
| Cyclohexane | 9.1 |
| N-Hexane | 14.9 |
| $H_2O$ | 16.8 |
| Surface Area, $m^2/g$ | 479 |

EXAMPLE 8

Twenty-five grams of solid crystal product from Example 7 were calcined in a flowing nitrogen atmospheres at 538° C. for 5 hours, followed by purging with 5% oxygen gas (balance $N_2$) for another 16 hours at 538° C.

Individual 3 g samples of the calcined material were ion-exchanged with 100 ml of 0.1N TEABr, TPABr and $LaCl_3$ solution separately. Each exchange was carried out at ambient temperature for 24 hours and repeated three times. The exchanged samples were collected by filtration, water-washed to be halide-free and dried. The compositions of the exchanged samples are tabulated below demonstrating the exchange capacity of the present crystalline silicate for different ions.

| Exchange Ions Ionic Composition, wt. % | TEA | TPA | La |
|---|---|---|---|
| Na | 0.095 | 0.089 | 0.063 |
| N | 0.30 | 0.38 | 0.03 |
| C | 2.89 | 3.63 | — |
| La | — | — | 1.04 |

EXAMPLE 9

The La-exchanged sample from Example 8 was sized to 14 to 25 mesh and then calcined in air at 538° C. for 3 hours. The calcined material had an Alpha Value of 173.

EXAMPLE 10

The calcined sample La-exchanged material from Example 9 was severely steamed at 649° C. in 100% steam for 2 hours. The steamed sample had an Alpha Value of 22, demonstrating that the zeolite had a very good stability under severe hydrothermal treatment.

EXAMPLE 11

This example illustrates the preparation of the present zeolite where X in the general formula, supra, is boron. Boric acid, 2.59 parts, was added to a solution containing 1 part of 45% KOH solution and 42.96 parts $H_2O$. To this was added 8.56 parts of Ultrasil silica, and the mixture was thoroughly homogenized. A 3.88 parts quantity of hexamethyleneimine was added to the mixture.

The reaction mixture had the following composition in mole ratios:
$SiO_2/B_2O_3 = 6.1$
$OH^-/SiO_2 = 0.06$
$H_2O/SiO_2 = 19.0$
$K/SiO_2 = 0.06$
$R/SiO_2 = 0.30$
where R is hexamethyleneimine.

The mixture was crystallized in a stainless steel reactor, with agitation, at 150° C. for 8 days. The crystalline product was filtered, washed with water and dried at 120° C. A portion of the product was calcined for 6 hours at 540° C. and found to have the following sorption capacities:

$H_2O$ (12 Torr): 11.7 wt.%
Cyclohexane (40 Torr): 7.5 wt.%
n-Hexane (40 Torr): 11.4 wt.%

The surface of the calcined crystalline material was measured (BET) to be 405 $m^2/g$.

The chemical composition of the uncalcined material was determined to be as follows:

| N | 1.94 wt. % |
|---|---|
| Na | 175 ppm |
| K | 0.60 wt. % |
| Boron | 1.04 wt. % |
| $Al_2O_3$ | 920 ppm |
| $SiO_2$ | 75.9 wt. % |
| Ash | 74.11 wt. % |
| $SiO_2/Al_2O_3$, molar ratio = 1406 | |
| $SiO_2/(Al + B)_2O_3$, molar ratio = 25.8 | |

EXAMPLE 12

A portion of the calcined crystalline product of Example 11 was treated with NH$_4$Cl and again calcined. The final crystalline product was tested in the Alpha Test and found to have Alpha Value of 1.

EXAMPLE 13

This example illustrates another preparation of the zeolite in which X of the general formula, supra, is boron. Boric acid, 2.23 parts, was added to a solution of 1 part of 50% NaOH solution and 73.89 parts H$_2$O. To this solution was added 15.29 parts of HiSil silica followed by 6.69 parts of hexamethyleneimine. The reaction mixture had the following composition in mole ratios:

| | |
|---|---|
| SiO$_2$/B$_2$O$_3$ = | 12.3 |
| OH$^-$/SiO$_2$ = | 0.056 |
| H$_2$O/SiO$_2$ = | 18.6 |
| K/SiO$_2$ = | 0.056 |
| R/SiO$_2$ = | 0.30 | where R is hexamethyleneimine.

The mixture was crystallized in a stainless steel reactor, with agitation, at 300° C. for 9 days. The crystalline product was filtered, washed with water and dried at 120° C. The sorption capacities of the calcined material (6 hours at 540° C.) were measured:

H$_2$O: 14.4 wt.%
Cyclohexane: 4.6 wt.%
n-Hexane: 14.0 wt.%

The surface area of the calcined crystalline material was measured to be 438m$^2$/g.

The chemical composition of the uncalcined material was determined to be as follows:

| Component | Wt. % |
|---|---|
| N | 2.48 |
| Na | 0.06 |
| Boron | 0.83 |
| Al$_2$O$_3$ | 0.50 |
| SiO$_2$ | 73.4 |
| SiO$_2$/Al$_2$O$_3$, molar ratio = 249 | |
| SiO$_2$/(Al + B)$_2$O$_3$, molar ratio = 28.2 | |

EXAMPLE 14

A portion of the calcined crystalline product of Example 13 was tested in the Alpha Test and found to have an Alpha Value of 5.

EXAMPLE 15

This example illustrates the use of a Lewis acid-, e.g. BF$_3$, promoted zeolite, e.g. having a Constraint Index of less than 5, as a catalyst in the alkylation of benzene with C$_{16}$ alpha olefin.

The zeolite was prepared by adding 4.49 parts quantity of hexamethyleneimine to a mixture containing 1.00 part sodium aluminate, 1.00 part 50% NaOH, 8.54 parts Ultrasil VN3 and 44.19 parts deionized H$_2$O. The reaction mixture was heated to 143° C. (290° F.) and stirred in an autoclave at that temperature for crystallization. After full crystallinity was achieved, the majority of the hexamethyleneimine was removed from the autoclave by controlled distillation and the zeolite crystals separated from the remaining liquid by filtration, washed with deionized H$_2$O and dried. The product crysals were MCM-22 having an X-ray diffraction pattern including the values of Tables A-D.

Prior to use in this example, the zeolite was calcined in nitrogen at 540° C., exchanged with aqueous ammonium nitrate, and calcined in air at 540° C.

A mixture of benzene and C$_{16}$ alpha olefin was continuously introduced into a 300 cc autoclave reactor loaded with 10g of the catalyst at a feed rate of 100 cc/hr, a mole ratio of benzene to olefin of 5:1, a temperature of about 68° F. and a pressure of 200 psig accompanied by continuous addition of BF$_3$ and a mixture of alkyl benzene product and unreacted benzene was continuously withdrawn from the reactor. Complete conversion of olefin unaccompanied by olefin oligomer was observed. Following separation of unreacted benzene from the alkyl benzene product, the latter was analyzed and the physical properties of a 600° F+ lube range fraction were measured, the results being set forth in Table H as follows:

TABLE H

| Alkyl Aromatic Lube Properties Obtained Using BF$_3$/MCM-22 Catalyst | |
|---|---|
| Catalyst System | BF$_3$/MCM-22 |
| Lube Properties | |
| Pour Point, °F. | −5 |
| KV at 40° C., cSt | 10.63 |
| KV at 100° C., cSt | 2.90 |
| Viscosity Index | 125 |
| Product Distribution, Wt. % | |
| Mono-alkyl benzene | 85 |
| Di-alkyl benzene | 15 |

EXAMPLE 16

TABLE I

| Alkyl Aromatic Lube Properties | |
|---|---|
| Pour Point, °F. | −30 |
| KV at 40° C., cSt | 10.41 |
| KV at 100° C., cSt | 2.82 |
| Viscosity Index | 118 |

While the above lube product had a slightly lower V.I. compared with the lube product of Example 15, the pour-point of the former was substantially less than the latter.

EXAMPLE 17

This example illustrates the alkylation of benzene with C$_{14}$ alpha olefin employing zeolite MCM-22 catalyst in the absence of a promoter and as such is outside the scope of this invention.

The alkylation reaction was conducted in a liter autoclave using 400g (2.02 moles) of C$_{14}$ alpha olefin and 79g (1.01 moles) of benzene (1:2 mole ratio of benzene to olefin) with 38g of MCM-22 catalyst at 400° F. for 6 hours under 400 psig nitrogen pressure. After decanting and filtering the catalyst, the total liquid product was distilled to obtain a 600° F.+ lube product, the properties of which are set forth in Table J as follows:

TABLE J

| Alkyl Aromatic Lube Properties | |
|---|---|
| Pour Point, °F. | −60 |
| KV at 40° C., cSt | 12.59 |
| K at 100° C., cSt | 3.15 |
| Viscosity Index | 113 |

Compared with the above lube product, the lube product of Example 16 was higher in V.I. and the temperature required to obtain it was much lower than that employed in this example.

EXAMPLE 18

This example illustrates the use of another Lewis acid-promoted zeolite, i.e., $BF_3$/zeolite Beta, in the process of the invention. In a manner similar to Example 15, a 1:1 mole ratio of toluene to $C_{16}$ alpha olefin was converted to alkylate over $BF_3$/zeolite Beta, the 600° F.+ lube product exhibiting the properties set forth in Table K as follows:

TABLE K
Properties of Alkyl Toluene Lube Product Obtained From $BF_3$/Zeolite Beta Catalyst System

| | |
|---|---|
| Pour Point, °F. | −5 |
| KV at 40° C., cSt | 12.7 |
| KV at 100° C., cSt | 3.18 |
| Viscosity Index | 114 |

What is claimed is:

1. A process for preparing long chain alkyl aromatic compounds which comprises contaccting at least one alkylatable aromatic compound with at least one alkylting agent possessing an alkylating aliphatic group having at least six carbon atoms under alkylation reaction conditions and in the presence of an alkylation catalyst to provide an alkylated aromatic product possessing at least one alkyl group derived from said alkylating agent, said catalyst comprising a Lewis acid-promoted zeolite possessing a Constraint Index of no greater than about 5 and said zeolite being characterized by an X-ray diffraction pattern including values substantially as set forth in Table A of the specification.

2. The process of claim 1 wherein the zeolite possesses a Constraint Index of not greater than about 3.

3. The process of claim 1 wherien the zeolite is characterized by an X-ray diffraction pattern including values substantially as set forth in Table B of the specification.

4. The process of claim 1 wherein the zeolite is characterized by an X-ray diffraction pattern including values substantially as set forth in Table C of the specification.

5. The process of claim 1 wherein the zeolite is characterized by an X-ray diffraction pattern including values substantially as set forth in Table D of the specification.

6. The process of claim 1 wherein the zeolite has a composition comprising the molar relationship $X_2O_3:(n)YO_2$, wherein n is at least about 10, X is a trivalent element and Y is a tetravalent element.

7. The process of claim 1 wherien the zeolite possesses equilibrium adsorption capacities of greater than about 4.5 wt. % for cyclohexane vapor and greater than about 10 wt. % for n-hexane vapor.

8. The process of claim 6 wherein X is selected from the group consisting of aluminum, boron, gallium and combinations thereof and Y is selected from the group consisting of silicon, germanium and combinations thereof.

9. The process of claim 6 wherein X comprises aluminum and Y comprises silicon.

10. The process of claim 1 wherein the zeolite has been treated to replace original cations, at least in part, with a cation or mixture of cations selected from the group consisting of hydrogen, hydrogen precursors, rare earth metals, and metals of Groups IIA, IIIA, IVA, IB, IIB, IIIB, IVB, VIB and VIII of the Periodic Table.

11. The process of claim 1 wherein the zeolite has been thermally treated at a temperature up to about 925° C. in the presence or absence of steam.

12. The process of claim 10 wherein the zeolite has been thermally treated at a temperature up to about 925° C. in the presence or absence of steam.

13. THe process of claim 1, wherein the Lewis acid is selected from the group consisting of $BF_3$, $BCl_3$, $SbF_3$ and $AlCl_3$.

14. The process of claim 1, wherein the alkylation is carried out in the opresence of small amounts of water and/or other material which produces water under alkylation reaction conditions to suppress catalyst aging.

15. The process of claim 1 wherein the alkylating aliphatic group contains at least about 8 carbon atoms.

16. The process of claim 1 wherein the alkylating aliphatic group contains at least about 12 carbon atoms.

17. The process of claim 1 wherein the alkylating agent is an olefin.

18. The process of claim 1 wherein the alkylating agent is an alcohol.

19. The process of claim 1 wherein the alkylating agent is an alkyl halide.

20. The process of claim 1 wherein the alkylatable armoatic compound is selected from the group consistign of benzene, xylene, toluene and 1,2,3,5-tetramethylbenzene.

21. The process of claim 1 wherein the alkylatable aromatic compound is selected from the group consisting of naphthalene, anthracene, naphthacene, perylene, coronene and phenanthrene.

22. The process of claim 1 wherein the alkylation reaction conditions include a temperature of from about −40° C. to about 250° C., a pressure of from about 0.2 to about 25 atmospheres, an WHSV of from about 0.01 to 500 hr$^{-1}$ and an alkylatable aromatic compound to alkylating agent mole ratio of from about 0.1:1 to 50:1.

23. The process of claim 1 wherein said zeolite is composited with a matrix material.

24. The process of claim 23 wherein said matrix material is selected from the group consisting of silica, alumina, zirconia, titania, beryllia, magnesia, thoria, and combinations thereof.

25. The process of claim 1 wherein said Lewis acid is continuously introduced into the alkylation reaction as a co-feed.

26. The process of claim 25 wherein the amount of Lewis acid introduced is sufficient to saturate the catalyst.

* * * * *